US00PP29605P2

(12) United States Plant Patent
Trees

(10) Patent No.: US PP29,605 P2
(45) Date of Patent: Aug. 14, 2018

(54) ***SALVIA* PLANT NAMED 'BALSALMYSTY'**

(50) Latin Name: ***Salvia* hybrid**
Varietal Denomination: Balsalmysty

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 45 days.

(21) Appl. No.: 15/530,703

(22) Filed: Feb. 16, 2017

(51) Int. Cl.
*A01H 5/02* (2018.01)

(52) U.S. Cl.
USPC ..... Plt./475

(58) Field of Classification Search
USPC ..... Plt./263.1, 475
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Salvia* plant named 'Balsalmysty', characterized by its dark violet-colored flowers, dark green-colored foliage, and moderately vigorous, upright-compact growth habit, is disclosed.

1 Drawing Sheet

Latin name of genus and species of plant claimed: *Salvia* hybrid.

Variety denomination: 'Balsalmysty'.

BACKGROUND OF THE INVENTION

The present invention relates to a new and distinct cultivar of *Salvia* plant botanically known as *Salvia* hybrid and hereinafter referred to by the cultivar name 'Balsalmysty'.

The new cultivar originated in a controlled breeding program in Guadalupe, Calif. during June 2012. The objective of the breeding program was the development of a *Salvia* cultivar having a dark flower color and an upright-compact growth habit.

The new *Salvia* cultivar was the result of a self-pollination of Mystic Spires Blue Improved 'Balsalmispim' U.S. application Ser. No. 15/530,700, concurrently filed application, characterized by its light violet-colored flowers, dark green-colored foliage, and vigorous, upright growth habit. The new cultivar was discovered and selected as a single flowering plant within the progeny of the above stated self-pollination during June 2013 in a controlled environment in Guadalupe, Calif.

Asexual reproduction of the new cultivar by terminal stem cuttings since June 2013 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsalmysty' as a new and distinct cultivar of *Salvia* plant:

1. Dark violet-colored flowers;
2. Dark green-colored foliage; and
3. Moderately vigorous, upright-compact growth habit.

Plants of the new cultivar differ from plants of the parent primarily in having a darker flower color, shorter inflorescences, and compact growth habit.

Of the many commercially available *Salvia* cultivars, the most similar in comparison to the new cultivar is 'Balsalmisp', U.S. Plant Pat. No. 18,054. However, in side by side comparisons, plants of the new cultivar differ from plants of 'Balsalmisp' in at least the following characteristics:

1. Plants of the new cultivar are shorter than plants of 'Balsalmisp';
2. Plants of the new cultivar have slightly darker colored flowers than plants of 'Balsalmisp'; and
3. Plants of the new cultivar have shorter inflorescences with fewer florets per inflorescence than plants of 'Balsalmisp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsalmysty'. The plants were grown in 4.5-inch pots for 8 weeks in a greenhouse in West Chicago, Ill. Plants were given one pinch at transplant.

DETAILED BOTANICAL DESCRIPTION

Figure 1:
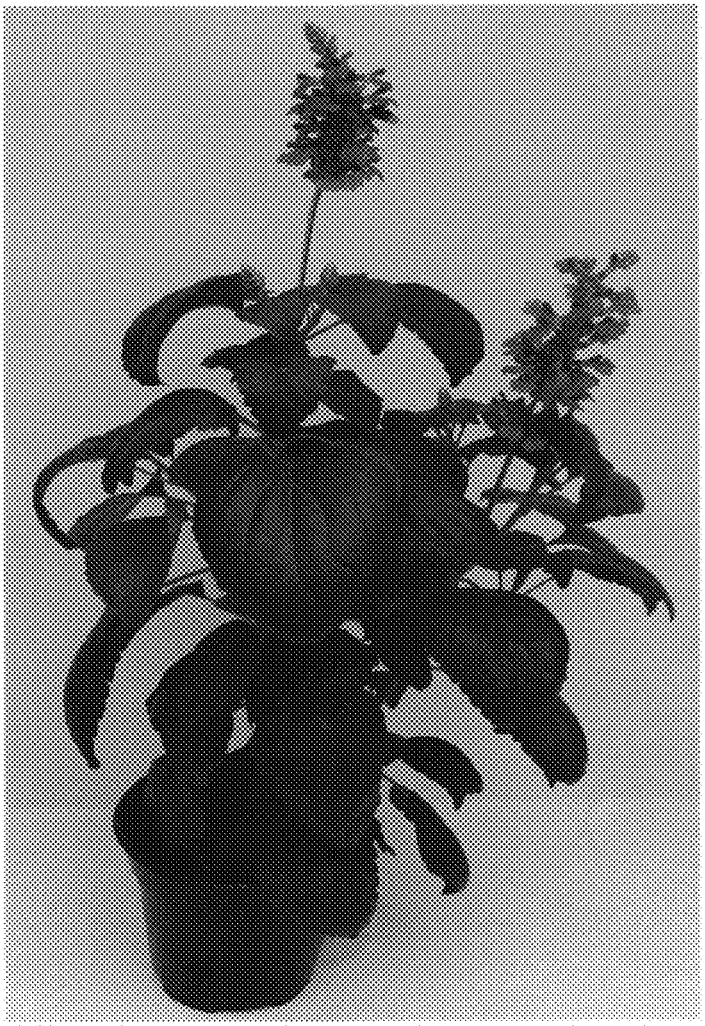
FIG. 1 illustrates a side view of the overall growth and flowering habit of 'Balsalmysty'.
Figure 2:
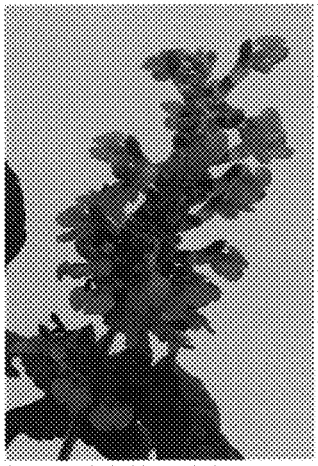
FIG. 2 illustrates a close-up view of an inflorescence of 'Balsalmysty'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2016 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 8 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Salvia* hybrid cultivar Balsalmysty.

Parentage:

*Female and male parent.*—Mystic Spires Blue Improved 'Balsalmispim', concurrently filed application.

Propagation:

*Type cutting.*—Terminal stem.

*Time to initiate roots.*—Approximately 5 to 8 days.

*Time to produce a rooted cutting.*—Approximately 21 to 42 days.

*Root description.*—Fine, fibrous.

*Rooting habit.*—Freely branching.

Plant description:

*Commercial crop time.*—Approximately 4 to 8 weeks from a rooted cutting to finish in a 10 cm pot.

*Growth habit and general appearance.*—Annual, moderately vigorous, upright-compact growth habit.

*Size.*—Height from soil level to top of plant plane: Approximately 39.0 cm. Width: Approximately 32.0 cm.

*Branching habit.*—Freely branching. Pinching enhances lateral branching. Quantity of branches per plant: Approximately 2.

*Branch.*—Shape: Square in cross section. Strength: Strong. Length to base of inflorescence: Approximately 18.0 cm. Diameter: Approximately 5.0 mm. Length of central internode: Approximately 4.0 cm. Texture: Densely pubescent with short, appressed hairs. Color of young and mature stems: 146C.

Foliage description:

*General description.*—Quantity of leaves per main branch: Approximately 10. Fragrance: Slight, sage-like. Form: Simple. Arrangement: Opposite.

*Leaves.*—Aspect: Petiole acute to perpendicular angle to stem, leaf blade becomes obtuse angle with age. Shape: Ovate. Margin: Crenate. Apex: Acute. Base: Obtuse. Venation pattern: Pinnate. Length of mature leaf: Approximately 9.5 cm. Width of mature leaf: Approximately 6.5 cm. Texture of upper surface: Sparsely pubescent with short, fine hairs, rugose. Texture of lower surface: Densely pubescent on venation only. Color of upper surface of young and mature foliage: 137A with 139A and venation of 146D. Color of lower surface of young and mature foliage: Closest to 137B with venation of 146D.

*Petiole.*—Length: Approximately 3.5 cm. Diameter: Approximately 2.0 mm. Texture: Densely pubescent. Color: 146D.

Flowering description:

*Flowering habit.*—'Balsalmysty' is freely flowering under outdoor growing conditions with substantially continuous blooming from spring through autumn and year-round in greenhouse environment.

*Lastingness of individual floret.*—Approximately 4 to 5 days.

Inflorescence description:

*General description.*—Type: Spikes in verticillaster arrangement, florets in clusters of nine, not persistent. Quantity of inflorescences per plant: Approximately 2. Fragrance: Faint, sweet. Length or height of inflorescence: Approximately 10.0 cm. Width of inflorescence: Approximately 4.5 cm. Quantity of fully-open flowers per inflorescence: Approximately 30, two to three per cluster open at one time.

*Peduncle.*—Shape: Square in cross section. Strength: Strong. Aspect: Erect. Length: Approximately 8.5 cm. Diameter: Approximately 3.0 mm. Texture: Densely pubescent with short, appressed hairs. Color: 146C.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 8.0 mm. Diameter: Approximately 3.0 mm. Texture: Densely pubescent. Color: Calyx of 138C and petal portion of N89A.

*Corolla.*—Shape: Bilabiate, lower lip having three lobes, base fused. Width: Approximately 1.1 cm. Length: Approximately 1.0 cm. Depth: Approximately 1.7 cm.

*Upper lip.*—Shape: Hooded. Margin: Entire. Apex: Rounded. Length from throat: Approximately 5.0 mm. Width: Approximately 3.0 mm. Texture of inner surface: Glabrous. Texture of outer surface: Densely pubescent. Color of pubescence: N89A. Color of inner surface when first and fully open: N88B. Color of outer surface when first and fully open: N88A, appears darker due to pubescence color.

*Lower lip.*—Shape of central lobe: Obovate. Margin: Entire. Apex of central lobe: Emarginate. Apex of lateral lobes: Rounded. Length from throat of central lobe: Approximately 1.1 cm. Width of central lobe: Approximately 1.1 cm. Length from throat of lateral lobes: Approximately 5.0 mm. Width of lateral lobes: Approximately 3.0 mm. Texture of upper surface: Glabrous. Texture of lower surface: Sparsely pubescent. Color of upper surface when first and fully open: N88B with central streaks of N88A. Color of lower surface when first and fully open: N88D with N88B near margins.

*Corolla tube.*—Length: Approximately 8.0 mm. Diameter at opening: Approximately 2.0 mm. Diameter at base: Approximately 1.0 mm. Texture of inner and outer surfaces: Glabrous. Color of inner surface when first and fully open: NN155D. Color of outer surface when first and fully open: NN155D with an overlay of N88C.

*Calyx.*—Shape: Tubular. Length: Approximately 6.0 mm. Diameter: Approximately 4.0 mm.

*Sepals.*—Quantity per flower: Fused into two lobes. Shape: Obovate. Apex: Upper lobe acute, lower lobe notched. Length: Approximately 6.0 mm. Width of lobes: Approximately 4.0 mm. Texture of inner surface: Glabrous. Texture of outer surface: Densely pubescent. Color of inner surface: 144A. Color of outer surface: 138A with N88A at apex, color appears lighter due to pubescence.

*Bracts.*—Quantity: One bract located at the base of each floret cluster. Length: Approximately 4.0 mm. Width: Approximately 5.0 mm. Texture of inner surface: Glabrous. Texture of outer surface: Densely pubescent. Color of inner surface: 144A. Color of outer surface: 138A, color appears lighter due to pubescence.

*Pedicel.*—Strength: Strong, flexible. Aspect: At an acute angle. Length: Approximately 1.0 mm. Diameter: Approximately 0.5 mm. Texture: Densely pubescent. Color: 138A, color appears lighter due to pubescence.

*Reproductive organs.*—Androecium: Stamen quantity: 2 per flower, dorsifixed, strongly curved. Stamen length: Approximately 7.0 mm. Filament length: Approximately 5.0 mm. Filament color: NN155D, opaque with an overlay of N88A. Anther shape: Oblong. Anther length: Approximately 2.0 mm. Anther color: N92B. Pollen amount: Abundant. Pollen color: 12B. Gynoecium: Pistil quantity: 1 per flower. Pistil length: Approximately 1.3 cm. Stigma shape: Cleft, two-parted. Stigma length: 2.0 mm. Stigma color: N88B. Style length: Approximately 9.0 mm. Style color: NN155D, opaque with an overlay of N88B near stigma. Style texture: Glabrous with a vertical line of feather-like pubescence of N88B extending from the stigma for approximately 3.0 mm. Ovary length: Approximately 2.0 mm. Ovary color: 154D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balsalmysty', substantially as herein illustrated and described.

* * * * *